US009862657B2

(12) United States Patent
Delferro et al.

(10) Patent No.: US 9,862,657 B2
(45) Date of Patent: Jan. 9, 2018

(54) METHODS FOR SELECTIVELY HYDROGENATING SUBSTITUTED ARENES WITH SUPPORTED ORGANOMETALLIC CATALYSTS

(71) Applicants: UOP LLC, Des Plaines, IL (US); NORTHWESTERN UNIVERSITY, Evanston, IL (US)

(72) Inventors: Massimiliano Delferro, Chicago, IL (US); Madelyn Marie Stalzer, Evanston, IL (US); Christopher P. Nicholas, Evanston, IL (US); Tobin Jay Marks, Evanston, IL (US); Alakananda Bhattacharyya, Glen Ellyn, IL (US)

(73) Assignees: UOP LLC, Des Plaines, IL (US); Northwestern University, Evanston, IL (US)

( * ) Notice: Subject to any disclaimer, the term of this patent is extended or adjusted under 35 U.S.C. 154(b) by 274 days.

(21) Appl. No.: 14/559,380

(22) Filed: Dec. 3, 2014

(65) Prior Publication Data
US 2016/0159709 A1 Jun. 9, 2016

(51) Int. Cl.
*C07C 5/10* (2006.01)
*B01J 31/00* (2006.01)
(Continued)

(52) U.S. Cl.
CPC ............... *C07C 5/10* (2013.01); *B01J 27/053* (2013.01); *B01J 31/00* (2013.01); *B01J 21/066* (2013.01);
(Continued)

(58) Field of Classification Search
CPC .... C07C 5/10; C07C 2531/12; C07C 2527/04
See application file for complete search history.

(56) References Cited

U.S. PATENT DOCUMENTS 3,869,522 A 3/1975 Van der Eijk
4,831,008 A 5/1989 Timmer et al.
(Continued)

FOREIGN PATENT DOCUMENTS

EP 2719455 A1 4/2014
PL 158739 B1 10/1992
WO 2014057417 A1 4/2014

OTHER PUBLICATIONS

Diehl et al., Determination of Benzene, Toluene, Ethylbenzene, and Xylenes in Gasolines by Gas Chromatography/Deuterium Isotope Dilution Fourier Transform Infrared Spectroscopy, Anal. Chem. (1993), 65, pp. 2493-2496.*
(Continued)

*Primary Examiner* — In Suk Bullock
*Assistant Examiner* — Youngsul Jeong (57) ABSTRACT

Methods for selectively hydrogenating substituted arenes with a supported organometallic hydrogenating catalyst are provided. An exemplary method includes contacting a substituted arene-containing reaction stream with hydrogen in the presence of a supported organometallic hydrogenating catalyst under reaction conditions effective to selectively hydrogenate the substituted arenes to the cis isomer with high selectivity. In this method, the supported organometallic hydrogenating catalyst includes a catalytically active organometallic species and a Brønsted acidic sulfated metal oxide support.

19 Claims, 4 Drawing Sheets

(51) Int. Cl.
*B01J 27/053* (2006.01)
*B01J 21/06* (2006.01)
(52) U.S. Cl.
CPC ...... *C07C 2527/04* (2013.01); *C07C 2531/22* (2013.01); *C07C 2601/14* (2017.05); *C07C 2602/28* (2017.05)

(56) References Cited

U.S. PATENT DOCUMENTS

| | | | |
|---|---|---|---|
| 5,344,970 | A | 9/1994 | Kolich |
| 6,235,918 | B1 * | 5/2001 | Marks .................... B01J 27/053 502/120 |
| 2012/0289740 | A1 | 11/2012 | Tan et al. |

OTHER PUBLICATIONS

Williams et al., Surface structural-chemical characterization of a single-site d0 heterogeneous arene hydrogenation catalyst having 100% active sites, Proceedings of the National Academy of Sciences of the United States of America (PNAS), Jan. 8, 2013, vol. 110, No. 2, pp. 413-418.*

Dyson, Arene hydrogenation by homogeneous catalysts: fact or fiction?, Laboratoire de Chimie Organométallique, Institut de Chimie Moléculaire et Biologique, Ecole Polytechnique Fédérale de Lausanne, EPFL-BCH, CH-1015 Lausanne, Switzerland, Received Mar. 24, 2003, Accepted Apr. 23, 2003, First published as an Advance Article on the web May 20, 2003.

Toppinen et al., Kinetics of the Liquid Phase Hydrogenation of Di- and Trisubstituted Alkylbenzenes over a Nickel Catalyst, Ind. Eng. Chem. Res. 1996, 35, 4424-4433.

Kubicka et al., Liquid-phase Hydrogenation of Diethylbenzenes, Catalysis Today 100 (2005) 453-456.

Stuhl et al., Catalytic Homogenous Hydrogenation of Arenes. 6. Reaction Scope for the q3-C3H5Co[P( OCH3)3]3 Catalyst, Journal of the American Chemical Society, 100:8, 2405-2410, Apr. 12, 1978.

Russell et al., Stereoselective Homogeneous Hydrogenation of Arenes to Cyclohexanes Catalysed by [Rh(YJ5-CsMes)C12ht, J.C. S. Chem. Comm., 427-428, 1977.

Hubert et al., Rh(0) Colloids Supported on TiO2: A Highly Active and Pertinent Tandem in Neat Water for the Hydrogenation of Aromatics, Green Chem., 2011, 13, 1766-1771.

Williams et al., "Synthesis, Characterization, and Heterogeneous Catalytic Implementation of Sulfated Alumina Nanoparticles, Arene Hydrogenation and Olefin Polymerization Properties of Supported Organozirconium Complexes", ACS Catalysis, vol. 1 (4), pp. 238-245, American Chemical Society, Feb. 21, 2011.

Nicholas et al., Synthesis, Spectroscopy, and Catalytic Properties of Cationic Organozirconium Adsorbates on "Super Acidic" Sulfated Alumina. "Single-Site" Heterogeneous Catalysts with Virtually 100% Active Sites. JACS Articles, Journal of American Chemical Society, vol. 125, pp. 4325-4331, American Chemical Society, Mar. 15, 2003.

Herzog et al., "2,4,6-Trimethylpyridine-bishydrofluoride; a novel fluorinating reagent for organo transition-metal alkyls", Chemical Communications, 1996, issue 1, pp. 29-30, Jan. 7, 1996.

Pellecchia et al., Single insertion of propene into a cationic zirconium(IV) complex: isolation and X-ray crystal structure of [(C5Me5,)Zr(CH2CHMeCH2Ph)(CH2h)]-[B(CH2Ph)(C6F5)3], Journal of Organometallic Chemistry, vol. 470, 1994.

Ahn et al., "Surface Organozirconium Electrophiles Activated by Chemisorption on "Super-Acidic" Sulfated Zirconia as Hydrogenation and Polymerization Catalysts. A Synthetic, Structural, and Mechanistic Catalytic Study", Organometallics 2002, vol. 21, pp. 1788-1806, published on Web Apr. 22, 2002.

* cited by examiner

METHODS FOR SELECTIVELY HYDROGENATING SUBSTITUTED ARENES WITH SUPPORTED ORGANOMETALLIC CATALYSTS

TECHNICAL FIELD

The technical field generally relates to methods for selectively hydrogenating substituted arenes, and more particularly relates to methods for selectively hydrogenating substituted arenes to the cis isomer.

BACKGROUND

Catalysts for the hydrogenation of substituted arenes to cyclohexanes are known and include standard hydrogenation catalysts such as $Pt/Al_2O_3$ and Pd/C, as well as organometallic hydrogenation catalysts, many of which are described by Dyson (*Dalton Trans.* 2003, 2964-74). Low levels of stereoselectivity have been achieved during hydrogenation of substituted arenes. For example, Russell, et. al. (*J. Chem. Soc. Chem. Commun.* 1977, 427-8) show 86% selectivity to cis-1,2-dimethylcyclohexane from o-xylene, 79% selectivity to cis-1,3-dimethylcyclohexane from m-xylene and 66% selectivity to cis-1,4-dimethylcyclohexane from p-xylene when using $[Rh(\eta^5-C_5Me_5)Cl_2]_2$ as the hydrogenation catalyst. Hubert, et. al. (*Green Chem.* 2011, 13, 1766-71) show pressure dependent selectivity to cis-substituted cyclohexanes, obtaining 90% selectivity to cis-1,2-dimethylcyclohexane from o-xylene at 1 bar $H_2$ but 95% selectivity at 30 bar $H_2$, 80% selectivity to cis-1,3-dimethylcyclohexane from m-xylene at 1 bar $H_2$ but 85% selectivity at 30 bar $H_2$ and 64% selectivity to cis-1,4-dimethylcyclohexane from p-xylene at 1 bar $H_2$ but 67% selectivity at 30 bar $H_2$ when using $Rh/TiO_2$ as the hydrogenation catalyst. Toppinen, et. al. (*Ind. Eng. Chem. Res.* 1996, 35, 4424-33) achieved selectivities of up to 55% to cis-1,2-dimethylcyclohexane from o-xylene, up to 77% to cis-1,3-dimethylcyclohexane from m-xylene, up to 48% to cis-1,4-dimethylcyclohexane from p-xylene, up to 80% to cis-1,3,5-trimethylcyclohexane from mesitylene, and up to 55% to cis-1-isopropyl-4-methylcyclohexane from p-cymene using $Ni/Al_2O_3$ as the catalyst. Kubicka, et. al. (*Catal. Today* 2005, 100, 453-6) show up to 44% selectivity to cis-1,2-diethylcyclohexane from 1,2-diethylbenzene, up to 77% selectivity to cis-1,3-diethylcyclohexane from 1,3-diethylbenzene and up to 55% selectivity to cis-1,4-dimethylcyclohexane from 1,4-diethylcyclohexane when using $Ni/Al_2O_3$ as the hydrogenation catalyst.

Muetterties and coworkers (*J. Am. Chem. Soc.* 1978, 100, 2405-10) have been able to demonstrate high selectivity to cis-substituted cyclohexanes from hydrogenation of substituted arenes, showing the ability to generate cis-substituted cyclohexanes from xylenes and trimethylbenzenes, but they utilize a homogeneous organometallic catalyst, $\eta^3$-$C_3H_5Co$ $[P(OCH_3)_3]_3$. Homogeneous catalysts are difficult to utilize in industrial processes as they are difficult to separate from the products of the reaction and thus to reuse.

Accordingly, it is desirable to provide methods for the hydrogenation of substituted arenes to cis-substituted cyclohexanes with increased selectivity to the cis-isomer. It is further desirable to provide methods for the hydrogenation of substituted arenes to cis-substituted cyclohexanes with selectivities greater than about 80% using a heterogeneous catalyst. Furthermore, other desirable features and characteristics of the methods contemplated herein will become apparent from the subsequent detailed description and the appended claims, taken in conjunction with the accompanying drawings and this background.

BRIEF SUMMARY

Methods for selectively hydrogenating substituted arenes to the cis isomer are provided herein. In accordance with an exemplary embodiment, a method for hydrogenation of substituted arenes includes contacting a reaction stream comprising one or more substituted arenes with hydrogen in the presence of a supported organometallic hydrogenating catalyst under reaction conditions effective to deliver hydrogen selectively to one face of the one or more substituted arenes yielding a product stream selective to cis-substituted cyclohexanes, wherein the supported organometallic hydrogenating catalyst comprises a catalytically active organometallic species and a Brønsted acidic sulfated metal oxide support.

In another exemplary embodiment a method for stereoselective hydrogenation of substituted arenes includes contacting a reaction stream comprising one or more substituted arenes with hydrogen in the presence of a supported organozirconium hydrogenating catalyst under reaction conditions effective to selectively hydrogenate the substituted arenes to cis-substituted cyclohexanes, wherein the supported organozirconium hydrogenating catalyst comprises a catalytically active organozirconium species and a Brønsted acidic sulfated metal oxide support.

Also provided herein a method for stereoselective hydrogenation of substituted arenes includes contacting a reaction stream comprising one or more substituted arenes with hydrogen in the presence of a heterogeneous hydrogenating catalyst under reaction conditions effective to deliver hydrogen selectively to one face of the substituted arenes, yielding a product stream comprising cis-substituted cyclohexanes, wherein selectivity to cis-substituted cyclohexanes is greater than 95%.

DETAILED DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

Various embodiments described herein are directed to methods for selectively hydrogenating substituted arenes by contacting with hydrogen in the presence of supported organo-zirconium catalysts. Single-site supported catalysts have attracted interest from both academic and industrial researchers due to their hybrid behavior in combining the advantages of traditionally hetero- and homogeneous systems.

The reaction pathway and kinetics of benzene hydrogenation catalysed by supported [$\eta^5$-$C_5(CH_3)_5$]Zr($CH_3$)$_2$ on sulfated aluminum oxide (Cp*ZrMe$_2$/AlS) using a combination of experimental ($^{13}$C-CPMAS NMR, EXAFS) and computational (DFT) methods have been reported and indicate the supported organozirconium moieties having an elongated Zr—$O_{AlS}$ distance of ~2.35(2) Å, which, when compared with the characteristic covalent Zr(IV)—OR bonds (1.94-2.01 Å)°, indicates a largely electrostatic, non-directional, ion pairing between the organometallic species and the surface. However, supported organometallic catalysts on super Brønsted acidic surfaces have not been known to be used to selectively hydrogenate arenes to the cis isomer. As used herein, the selectivity of a catalyst refers to a catalyst's ability to preferentially hydrogenate the substituted arenes to the cis isomer. In some embodiments, the selectivity is greater than about 80%, such as greater than about 90%, greater than about 95%, greater than about 99% or greater than about 99.5%. In some embodiments, essentially 100% selectivity to the cis isomer product is achieved.

As used herein, essentially 100% selectivity is meant to describe the ability to differentiate the present value from 100%. Essentially 100% indicates the current value cannot be distinguished from 100%. Different methods of determining the composition of a stream (for example, to determine selectivity) have different detection limits, that is, the amount of compound required to elicit a response from the detector such that signal is distinguishable from noise. For example, GC-MS has a lower detection limit than does NMR. In practice, essentially 100% may indicate greater than about 99% or greater than about 99.5% or greater than about 99.9% or greater than about 99.95%.

The organometallic catalysts used in the methods herein contain a metal atom at the catalytic center with multiple ligand groups attached thereto. Without wishing to be bound by theory, it is believed that the size and identity of the ligand groups attached to the metallic catalytic center, the identity of the metal center and the support affects catalytic behavior in the supported catalysts. Specifically, the ligands define the space surrounding the catalytic center that is available to an arene while undergoing hydrogenation by affecting the distance between catalytic center and the surface of the support as well as the electronic environment of the catalytically active organometallic species.

Described herein are methods for the selective hydrogenation of substituted arenes to the cis isomer by contacting the substituted arenes with hydrogen in the presence of a supported organometallic catalyst under reaction conditions effective to deliver hydrogen selectively to one face of the substituted arenes.

Figure 1:
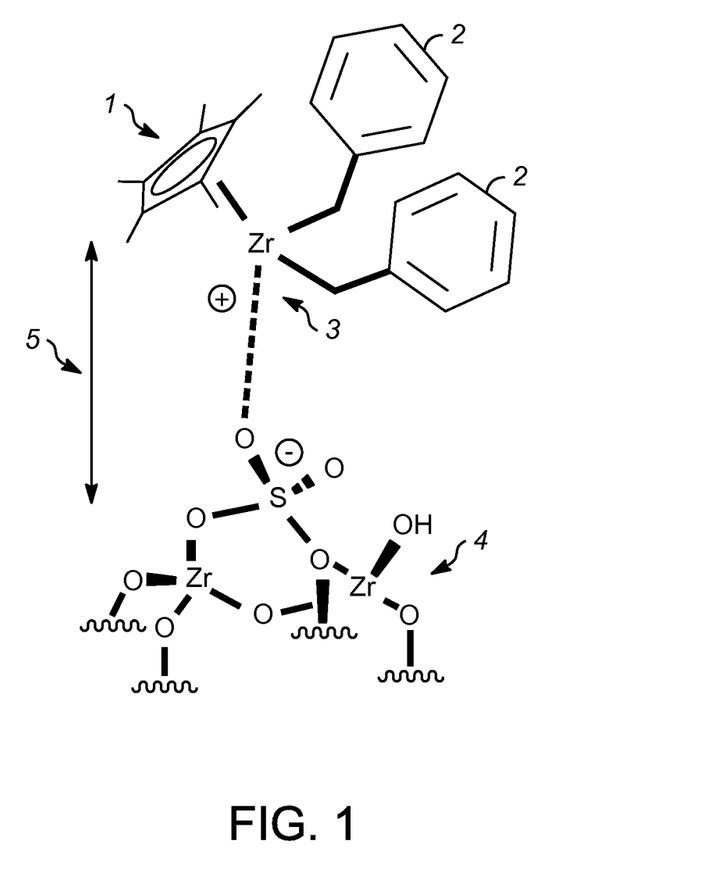
FIG. 1 is an illustration of a chemical structure of a chemisorbed $Cp^*ZrBz_2$ on highly Brønsted acidic sulfated metal oxide according to an exemplary embodiment.

The catalytically active metal center of the organometallic catalyst may be Ti, Zr, Hf, Nb, Ta, Mo, W, Pd or Pt, but is preferably Ti, Zr or Hf and most preferably is Zr. In some embodiments the supported organometallic catalyst is an organo-zirconium catalyst attached to a support. In some embodiments, the supported organo-zirconium catalyst is a supported version of an unsupported organo-zirconium catalyst with the general formula of $Cp^{\#}_c ZrR_r$, where $Cp^{\#}$ indicates a cyclopentadienyl ligand such as cyclopentadienyl (Cp), pentamethylcyclopentadienyl (Cp*), a cyclopentadienyl radical substituted with alkyl or trimethylsilyl groups such as 1,2-dimethylcyclopentadienyl (Cp"), or a fused cyclopentadienyl radical such as indenyl; c is from 0 to 2; Zr is zirconium; R is an alkyl or aromatic ligand selected from the group consisting of methyl or substituted methyl (Me), benzyl or substituted benzyl (Bz), phenyl or substituted phenyl (Ph), 2,2-dimethylpropyl (also known as neopentyl, Np) or substituted 2,2-dimethylpropyl, trimethylsilylmethyl (also known as neosilyl, Ns) or substituted trimethylsilylmethyl, and 2,2-dimethylethylbenzyl (also known as neophyl, Nph) or substituted 2,2-dimethylethylbenzyl; and r is determined by the equation r=4−c. In some embodiments, c is 1. In some specific embodiments, the supported organo-zirconium catalyst is a supported version of an unsupported organo-zirconium catalyst selected from the group consisting of Cp*ZrMe$_3$, Cp*ZrBz$_3$, Cp*ZrPh$_3$, Cp$_2$ZrMe$_2$, and ZrBz$_4$. In an exemplary embodiment, the supported organo-zirconium catalyst is a supported version of the unsupported organo-zirconium catalyst Cp*ZrBz$_3$. This is illustrated in FIG. 1, which shows an illustration of a chemical structure of a chemisorbed Cp*ZrBz$_2$ on highly Brønsted acidic sulfated metal oxide. The species shown in FIG. 1 comprises a catalytic center with a Cp* ligand 1, a benzyl ligand 2, a catalytically active metal center Zr, 3, and sulfated zirconia, 4, a Bronsted acidic sulfated metal oxide support. Without wishing to be bound by theory, it is believed that an alkyl ligand reacts with an acidic hydroxyl of the Bronsted acidic support to yield a mole of alkane and the cationic catalytically active supported organometallic species. The distance, 5, between the support 4 and the metal center 3, may be an important parameter to achieving high cis selectivity in the preferential hydrogenation of substituted arenes. Thus, in some embodiments, the distance between the catalytic center 3 and the support surface 4 is greater than about 2.37 Å, such as greater than or equal to about 2.40 Å.

In some embodiments, the organometallic catalytic materials are adsorbed on a support material comprising a super Brønsted acidic surface (SBAS). Discussion of super Brønsted acidic surfaces may be found in the art, e.g., in Ahn, et. al. *Organometallics,* 2002, 21, 1788-1806. In some embodiments, the SBAS support material comprises sulfated alumina (AlS), sulfated zirconia (ZrS) or tungstated zirconia (ZrW). In some embodiments, the SBAS support material comprises sulfated zirconia (ZrS). Two phases of zirconia (ZrO$_2$) are commonly seen, a tetragonal phase and a monoclinic phase, often referred to as baddeleyite. In some embodiments, the content of tetragonal zirconia in the sulfated zirconia support is greater than 60%, or greater than 75% or greater than 85%. Thus, in some embodiments, the supported organo-zirconium catalyst has the general formula of $Cp^{\#}_c ZrR_r$/SBAS, where $Cp^{\#}_c ZrR_r$ is as defined above, except r is determined by the equation r=3−c; and SBAS is a super Brønsted acidic surface (SBAS). In some embodiments, the supported organometallic catalysts are selected from the group consisting of Cp*ZrMe$_2$/ZrS, ZrBz$_3$/ZrS, Cp*ZrPh$_2$/ZrS, and Cp*ZrBz$_2$/ZrS.

The reaction stream as described herein comprises one or more substituted arenes. In some embodiments, the one or more substituted arenes are selected from the group consisting of di-alkyl arenes, tri-alkyl arenes, bicyclic arenes, and/or mixtures thereof. In some embodiments, the one or more substituted arenes are selected from the group consisting of xylenes, trimethylbenzenes, naphthalenes, and/or mixtures thereof.

As used herein, di-alkylarenes may include any arene with two alkyl groups of the formula $C_nH_{2n+1}$ where n is from 1 to 4; examples include xylenes, diethylbenzenes, and methylethylbenzenes. In some embodiments, the two alkyl groups are the same or different. Xylenes may include any or all of the xylene isomers ortho-xylene, meta-xylene and para-xylene. Tri-alkylarenes may include any arene with three alkyl groups of the formula $C_nH_{2n+1}$ where n is from 1 to 4; examples include trimethylbenzenes, triethylbenzenes, and dimethylethylbenzenes. Trimethylbenzenes may include 1,2,3-trimethylbenzene, 1,2,4-trimethylbenzene, 1,3,5-trimethylbenzene (mesitylene), and/or mixtures thereof. Bicyclic arenes may include arenes included in fused-ring systems. Examples include naphthalenes, indenes, indane, methylated derivatives of indane such as 2-methylindane or 5-methylindane, and tetralin. Indenes may include indene and methylated derivatives of indene such as 1-methylindene and 2-methylindene. Naphthalenes may include naphthalene, 1,2,3,4-tetrahydronaphthalene (tetralin) and methylated derivatives of naphthalenes such as 2-methylnaphthalene. In some embodiments, the reaction stream comprises about 5 to about 100 wt. % substituted arenes, such as about 50 to about 99.95 wt. % substituted arenes.

The methods as described herein stereoselectively hydrogenate arenes to cis substituted cyclohexanes including cis-1,2-dimethylcyclohexane, cis-1,3-dimethylcyclohexane, cis-1,4-dimethylcyclohexane, cis-1,2-diethylcyclohexane, cis-1,2-ethylmethylcyclohexane, cis-1,3,5-trimethylcyclohexane, cis-1,2,3-trimethylcyclohexane, cis-1,2,4-trimethylcyclohexane, cis-decalin, and/or mixtures thereof.

The catalysts used herein deliver hydrogen selectively to one face of the one or more substituted arenes yielding a product stream selective to cis-substituted cyclohexanes. Substituted arenes are flat planar molecules containing two faces (up and down) to which hydrogen may be added to convert the arene to a cyclohexane. Catalysts for the hydrogenation of arenes deliver hydrogen to one face, or to both faces of the substituted arene. To hydrogenate a substituted arene to a cis-substituted cyclohexane, the hydrogen must be delivered to only one face of the substituted arene (up, up, up or down, down, down for the three double bonds in an arene). If hydrogen is delivered to more than one face of the substituted arene (up, up, down; up, down, up; etc.), then a variety of trans-substituted cyclohexanes will result.

The substitution pattern of the resulting cis-substituted cyclohexanes is determined by the substitution pattern of the substituted arene. In an exemplary embodiment, the cis-substituted cyclohexanes are selected from the group consisting of cis-di-alkylcyclohexanes, cis-tri-alkylcyclohexanes, cis-bicyclic cyclohexanes, and/or mixtures thereof. In an exemplary embodiment, the cis-substituted cyclohexanes are selected from the group consisting of cis-dimethylcyclohexanes, cis-trimethylcyclohexanes, cis-decalins, and/or mixtures thereof.

As used herein, cis-di-alkylcyclohexanes may include any cyclohexane with two cis-alkyl groups of the formula $C_nH_{2n+1}$ where n is from 1 to 4; examples include cis-dimethylcyclohexanes, cis-diethylcyclohexanes, and cis-methylethylcyclohexanes. Cis-dialkylcyclohexanes include cis-1,2-diethylcyclohexane and cis-1,2-ethylmethylcyclohexane. In an exemplary embodiment, the two alkyl groups may be the same or different. Cis-dimethylcyclohexanes may include any or all of the cis-dimethylcyclohexane isomers cis-1,2-dimethylcyclohexane, cis-1,3-dimethylcyclohexane, and cis-1,4-dimethylcyclohexane. Cis-tri-alkylcyclohexanes may include any cyclohexane with three cis-alkyl groups of the formula $C_nH_{2n+1}$ where n is from 1 to 4; examples include cis-trimethylcyclohexanes, cis-triethylcyclohexanes, and cis-dimethylethylcyclohexanes. Cis-trimethylcyclohexanes may include cis-1,2,3-trimethylcyclohexane, cis-1,2,4-trimethylcyclohexane, cis-1,3,5-trimethylcyclohexane, and/or mixtures thereof. Cis-bicyclic cyclohexanes may include cyclohexanes included in fused-ring systems. Examples include cis-decalins and cis-perhydroindans. Cis-decalins may include methylated derivatives of cis-decalin, such as cis-2-methyl-decalin. Cis-perhydroindans may include cis-perhydroindan and methylated derivatives thereof, such as 1-methyl-cis-perhydroindan and 2-methyl-cis-perhydroindan.

The methods described herein accomplish stereoselective hydrogenation of substituted arenes under generally mild reaction conditions. The particulars of the reaction conditions may vary somewhat depending on the particular composition of the reaction stream and the physical parameters of the reaction system. Determination of suitable reaction conditions (including reaction stream flow rate, hydrogen flow rate, input temperature, catalyst temperature, etc.) may be determined by one of skill in the art. In some embodiments, these conditions may include a temperature of from about room temperature to about 150° C., or from about 20° C. to about 85° C., a pressure of from about 1 atm to about 20 atm or from about 1 atm to about 10 atm and a hydrogen:total arene ratio of from about 0.1 to about 100.

Those having skill in the art, with the knowledge gained from the methods as contemplated herein, will recognize that various changes could be made in the methods described herein without departing from the scope of the embodiments contemplated herein. Mechanisms used to explain theoretical or observed phenomena or results, shall be interpreted as illustrative only and not limiting in any way the scope of the appended claims.

The following examples include representative methods of selective hydrogenation of substituted arenes to cis-substituted cyclohexanes. These examples are not to be construed as limiting as other equivalent embodiments will be apparent in view of the method contemplated herein and appended claims.

EXAMPLES

General

Unless otherwise noted, the catalytic hydrogenation studies for supported catalysts described in the Examples were performed according to the following protocol. All procedures for air- and moisture-sensitive compounds were carried out with rigorous exclusion of $O_2$ and moisture in flame or oven-dried Schlenk-type glassware interfaced to a dual-manifold Schlenk line or a high-vacuum ($10^{-5}$-$10^{-6}$ Torr) line, or in a nitrogen-filled M-Braun glovebox with a high capacity recirculator (<1 ppm O2). Argon (Airgas, pre-purified) was purified by passage through MnO/vermiculite and Davidson 4 A molecular sieve columns Oxygen (Airgas) was purified by passage through Drierite (Hammond Co.). All hydrocarbon solvents (n-pentane, benzene, and alkylarene substrates) were distilled from Na/K alloy and stored in resealable flasks.

All other starting materials were purchased from Aldrich Chemical Co. or Strem Chemicals Inc. and used without further purification unless otherwise noted. $C_6D_6$ was purchased from Cambridge Isotope Laboratories (>99 atom % D), dried over Na/K alloy, and stored in resealable flasks. The organometallic complex Cp*ZrBz$_3$ (1) was prepared by the procedure described in Wolczanski, P. T.; Bercaw, J. E. *Organometallics* 1982, 1, 793-799. The supports sulfated Zirconia (ZrS) were prepared via the procedures described in U.S. Pat. No. 4,956,519 without the Fe or Mn nitrate in solution A. The product of the synthesis was then extruded with alumina at 80/20 ratio of $ZrO_2/Al_2O_3$ followed by a 500° C. calcination for 4 hours. ZrS was 70% tetragonal and 30% monoclinic and composed of Zr 58.0%, Hf 1.11%, Fe 0.02%, Al 10.2%, S 2.02%. The surface area was determined to be 141 m$^2$/g by BET isotherm methods and 219 m$^2$/g by Langmuir isotherm method. The total pore volume was 0.166 mL/G, with an average pore diameter of 47 Å. Finally, it was activated by heating to 450° C. under high vacuum (10$^{-6}$ torr) for 1 h, then storing at −40° C. under nitrogen. Supported organozirconium catalysts on ZrS (Cp*ZrBz2/ZrS) were prepared by utilization of a two-sided fritted reaction vessel where pentane was condensed onto carefully measured quantities of the organometallic complex and of acidic inorganic oxide. The resulting slurry was stirred at 25° C. for 1 h, then filtered. The impregnated support was collected on the frit and washed three times with pentane, then dried in vacuo for 1 h. The prepared catalysts were stored in a sealed container under a dry N$_2$ atmosphere at −40° C. until used. In general, 25 mL of pentane is used for the reaction of 50 mg organometallic complex and 2 g sulfated zirconia and 20 mL of pentane is used per wash. If more than the saturation coverage of 5.8×10$^{-6}$ mol organometallic species/g ZrS was used, excess complex could be seen on the opposite side of the fritted vessel after washing. Commercial palladium on carbon (Pd/C; 10 wt % Pd) was purchased from Aldrich Chemical Co.

Solution NMR spectra were measured on a Varian Inova 500 spectrometer (FT, 500 MHz, $^1$H; 125 MHz, $^{13}$C). Air sensitive $^1$H and $^{13}$C NMR experiments were run using sample tubes fitted with a Teflon valve (J-Young). Solid state $^{13}$C CPMAS experiments were recorded on a Varian 400 spectrometer (FT, 100 MHz, $^{13}$C). Air-sensitive samples were loaded into a zirconia rotor in the glovebox, then sealed with a Teflon cap. Routine organozirconium adsorbate spectra were recorded with a cross-polarization time of 2 ms, a recycle time of 5 s, and a spinning rate of 10 k. GC/MS data was collected on a Waters GC-TOF equipped with a DB5 30 m column Ionization was achieved by electron impact ionization.

Arene Hydrogenation Using Supported Organozirconium Catalysts

Unless otherwise noted, the catalytic hydrogenation studies for supported organozirconium catalysts described in the Examples were performed according to the following protocol. Heavy wall, high pressure, screw top flasks fitted with a Teflon screw cap that were modified with a Swagelok ball valve were used as the reaction vessels. In a typical experiment with a liquid substrate, the flask was charged with 50 mg of supported catalyst and 2 mL of substrate in the glovebox. If the substrate was a solid, 1 g of substrate was used and 2 mL of n-pentane was added as a solvent. The sealed vessel was then transferred to a high vacuum line, evacuated at −78° C., then allowed to warm to 25° C. and pressurized with 7 atm of H$_2$. The reaction mixture was allowed to stir vigorously for 1 hr and the product was analyzed by $^1$H NMR and GC/MS.

Arene Hydrogenation Using Commercial Pd/C Catalysts

Unless otherwise noted, the catalytic hydrogenation studies for commercial Pd/C catalysts described in the Examples were performed according to the following protocol. Heavy wall, high pressure, screw top flasks fitted with a Teflon screw cap that has been modified with a Swagelok ball valve were used as the reaction vessels. In a typical experiment with a liquid substrate, the flask was charged with 1.0 g of Pd/C (10 wt % Pd), 2 mL of substrate in the glovebox, and 2 mL of hexane. The sealed vessel was then transferred to a high vacuum line, evacuated at −78° C., then allowed to warm to 25° C. and pressurized with 1 atm of H$_2$. The reaction mixture was allowed to stir vigorously for 1 hr and the product was analyzed by $^1$H NMR and GC/MS.

Example 1

Di-Alkyl Arene Hydrogenation

The catalysts were tested with o, m, and p-xylene, in order to determine whether o, m, and p-xylene substrates could be hydrogenated with complete stereoselective control. The substrates were successfully hydrogenated using Cp*ZrBz$_2$/ZrS as the catalyst and found to be stereo-pure by GC-MS and $^1$H NMR to the detection limit. For every case, the cis isomer was the sole product. These substrates were also hydrogenated with commercially available Pd/C so as to provide a comparison, and this catalyst was found to not only have poor turnover frequency, but also gave mixtures of stereoisomers of these products.

Figure 2A:
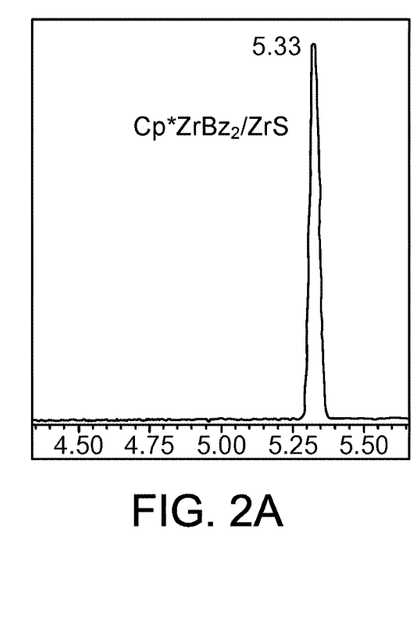
FIGS. 2A, B, C, D, E, and F show GC-MS chromatograms showing products from arene hydrogenation using $Cp^*ZrBz_2/ZrS$ in comparison to using commercial Pd/C according to Example 1.
Figure 2B:
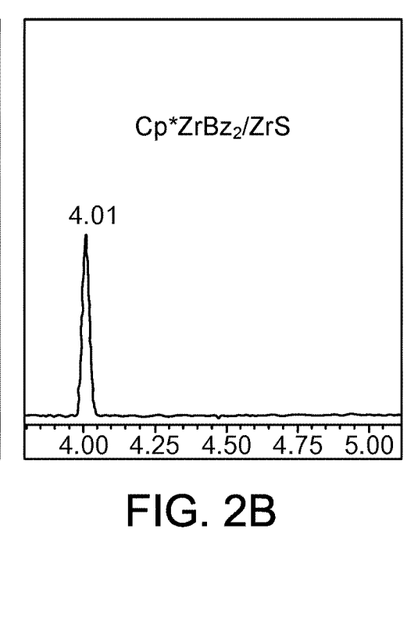
Figure 2C:
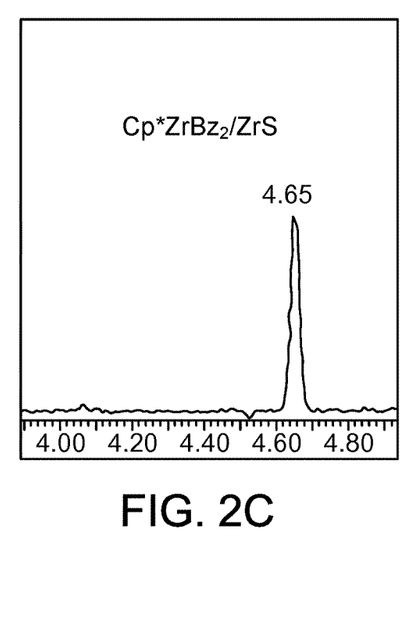
Figure 2D:
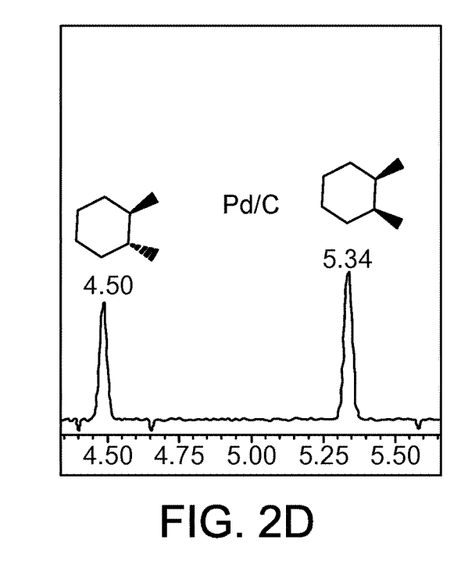
Figure 2E:
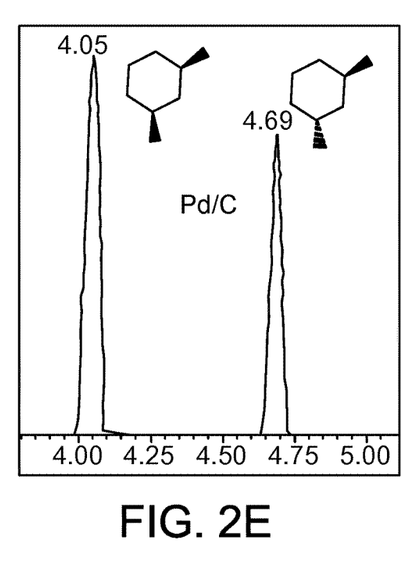
Figure 2F:
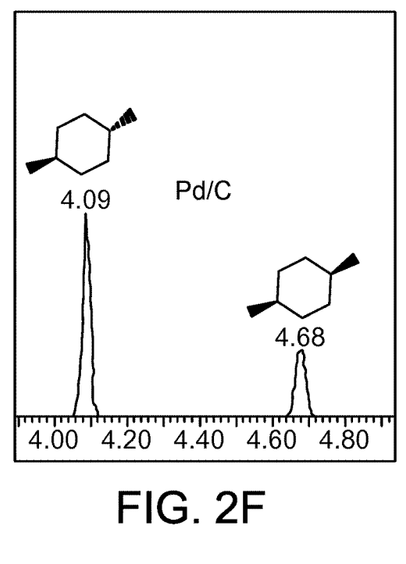

FIGS. 2A, B, C, D, E and F show GC-MS chromatograms run on DB-5 column, 40° C. to 70° C. at 3° C./min Chromatograms FIGS. 2A, 2B and 2C are dimethylcyclohexane products from Cp*ZrBz$_2$/ZrS mediated xylenes hydrogenation. Chromatograms FIGS. 2D, 2E and 2F are dimethylcyclohexane products from Pd/C mediated xylenes hydrogenation. Substrates are as follows: A,D. o-xylene; B,E. m-xylene; and C,F. p-xylene.

Other di-alkyl arenes were successfully hydrogenated using the Cp*ZrBz$_2$/ZrS as seen in Table 1 below and compared to results obtained with the comparative Pd/C catalyst.

TABLE 1

| | | Hydrogenation data for di-alkyl arenes | | | |
|---|---|---|---|---|---|
| Substrates[a] | Product | Cp*ZrBz$_2$/ZrS TOF (h$^{-1}$)[a,b] | Cp*ZrBz$_2$/ZrS Selectivity[c] | Pd/C TOF (h$^{-1}$)[d,e] | Pd/C Selectivity[c] |
| o-xylene | cis-1,2-dimethylcyclohexane | 1000 | >99.9 | <1 | 62 |
| m-xylene | cis-1,3-dimethylcyclohexane | 470 | >99.9 | <1 | 62[f] |

TABLE 1-continued

Hydrogenation data for di-alkyl arenes

| Substrates[a] | Product | Cp*ZrBz$_2$/ZrS TOF (h$^{-1}$)[a,b] | Cp*ZrBz$_2$/ZrS Selectivity[c] | Pd/C TOF (h$^{-1}$)[d,e] | Pd/C Selectivity[c] |
|---|---|---|---|---|---|
| 1,4-dimethylbenzene | cis-1,4-dimethylcyclohexane | 120 | >99.9 | <1 | 31 |
| 1,2-diethylbenzene | cis-1,2-diethylcyclohexane | 425 | >99.9 | <1 | 31 |
| 1-ethyl-2-methylbenzene | cis-1-ethyl-2-methylcyclohexane | 36 | >99.9 | <1 | 61 |

[a][Catalyst] = 50 mg, loading = 0.24 wt % Zr, 1h, 25° C., 7 atm H$_2$, measured by $^1$H NMR.
[b]TOF (mol substrate)(mol Zr)$^{-1}$h$^{-1}$
[c]Determined by GC-MS
[d][Catalyst] = 10 mol %, 2h, 25° C., 1 atm H$_2$
[e]TOF (mol substrate)(mol Pd)$^{-1}$h$^{-1}$
[f]run for 16h Example 2

Tri-Alkyl Arene Hydrogenation

Tri-alkyl arenes were successfully hydrogenated using the Cp*ZrBz$_2$/ZrS as seen in Table 2 below. The substrates were successfully hydrogenated using Cp*ZrBz$_2$/ZrS as the catalyst and found to be stereo-pure by GC-MS and $^1$H NMR to the detection limit. For every case, the cis isomer was the sole product. These substrates were also hydrogenated with commercially available Pd/C so as to provide a comparison, and this catalyst was found to not only have poor turnover frequency, but also gave mixtures of stereoisomers of these products.

Figure 3A:
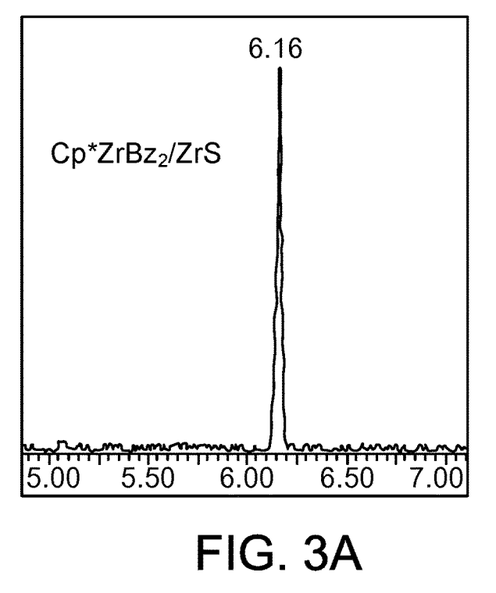
FIGS. 3A and B show GC-MS chromatograms showing products from arene hydrogenation using $Cp^*ZrBz_2/ZrS$ in comparison to using commercial Pd/C according to Example 2.
Figure 3B:
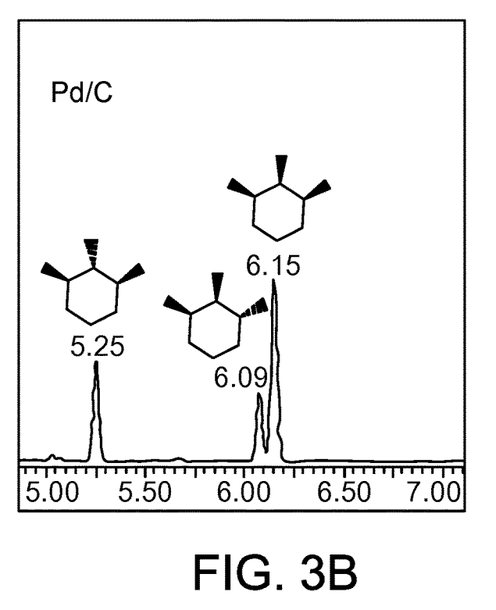

FIGS. 3A and B show GC-MS chromatograms run on DB-5 column, 40° C. to 70° C. at 3° C./min Chromatogram FIG. 3A is the 1,2,3-trimethylcyclohexane product from Cp*ZrBz$_2$/ZrS mediated 1,2,3-trimethylbenzene hydrogenation. Chromatogram FIG. 3B is the 1,2,3-trimethylcyclohexane products from Pd/C mediated 1,2,3-trimethylbenzene hydrogenation.

Example 3

Bicyclic (Fused Ring) Arene Hydrogenation

Bicyclic arenes (fused ring substrates) were successfully hydrogenated using Cp*ZrBz$_2$/ZrS as the catalyst with essentially 100% stereoselectivity to the cis isomer.

TABLE 2

Hydrogenation data for tri-alkyl arenes

| Substrates[a] | Product | Cp*ZrBz$_2$/ZrS TOF (h$^{-1}$)[a,b] | Cp*ZrBz$_2$/ZrS Selectivity[c] | Pd/C TOF (h$^{-1}$)[d,e] | Pd/C Selectivity[c] |
|---|---|---|---|---|---|
| 1,3,5-trimethylbenzene | cis-1,3,5-trimethylcyclohexane | 67 | >99.9 | <1 | 84 |
| 1,2,3-trimethylbenzene | cis-1,2,3-trimethylcyclohexane | 130 | >99.9 | <<1 | 54 |
| 1,2,4-trimethylbenzene | cis-1,2,4-trimethylcyclohexane | 16 | >99.9 | <1 | 49 |

[a][Catalyst] = 50 mg, loading = 0.24 wt % Zr, 1h, 25° C., 7 atm H$_2$, measured by $^1$H NMR.
[b]TOF (mol substrate)(mol Zr)$^{-1}$h$^{-1}$
[c]Determined by GC-MS
[d][Catalyst] = 10 mol %, 2h, 25° C., 1 atm H$_2$
[e]TOF (mol substrate)(mol Pd)$^{-1}$h$^{-1}$

TABLE 3

Hydrogenation data for bicyclic (fused ring) arenes.

| Substrate[a] | Product | TOF[b] (h$^{-1}$) | Selectivity |
|---|---|---|---|
| naphthalene | decalin | 20 | >99.9 |
| tetralin | decalin | 40 | >99.9 |
| 2,6-dimethylnaphthalene | One Stereoisomer | <10 | >99.9 |
| biphenyl | bicyclohexyl | 12 | >99.9 |

[a][Catalyst] = 50 mg, loading = 0.24 wt % Zr, 1h, 25° C., 7 atm H$_2$, measured by $^1$H NMR.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the methods as contemplated herein in any way. Rather, the foregoing detailed description will provide those skilled in the art with a convenient road map for implementing an exemplary embodiment of the method as contemplated herein. It being understood that various changes may be made in the function and arrangement of elements described in an exemplary embodiment without departing from the scope of the methods as contemplated herein as set forth in the appended claims.

What is claimed is:

1. A method for hydrogenation of substituted arenes comprising the step of:
   contacting a reaction stream comprising one or more substituted arenes with hydrogen in the presence of a supported organometallic hydrogenating catalyst under reaction conditions effective to deliver hydrogen selectively to one face of the one or more substituted arenes yielding a product stream, wherein the product stream is selective to cis-substituted cyclohexanes when the reaction stream comprises two or more substituted arenes,
   wherein the supported organometallic hydrogenating catalyst comprises a catalytically active organometallic species with the general formula of $Cp^{\#}_c ZrR_r$, and a Brønsted acidic sulfated metal oxide support,
   where $Cp^{\#}$ indicates a cyclopentadienyl ligand selected from the group consisting of cyclopentadienyl (Cp), pentamethylcyclopentadienyl (Cp*), a cyclopentadienyl radical substituted with alkyl or trimethylsilyl groups, and a fused cyclopentadienyl radical; c is from 1 to 2; Zr is zirconium; R is an alkyl or aromatic ligand selected from the group consisting of benzyl or substituted benzyl (Bz), phenyl or substituted phenyl (Ph), 2,2-dimethylpropyl (neopentyl) or substituted 2,2-dimethylpropyl, trimethylsilylmethyl (neosilyl) or substituted trimethylsilylmethyl, and 2,2-dimethylethylbenzyl (neophyl) or substituted 2,2-dimethylethylbenzyl; and r is determined by the equation r=4−c.

2. The method of claim 1, wherein the substituted arenes are selected from the group consisting of di-alkyl arenes, tri-alkyl arenes, bicyclic arenes, and/or mixtures thereof.

3. The method of claim 2, wherein the substituted arenes are selected from the group consisting of xylenes, trimethylbenzenes, naphthalenes, and/or mixtures thereof.

4. The method of claim 1, wherein the cis-substituted cyclohexanes are selected from the group consisting of cis-di-alkylcyclohexanes, cis-tri-alkylcyclohexanes, cis-bicyclic cyclohexanes, and/or mixtures thereof.

5. The method of claim 1, wherein the supported organometallic hydrogenating catalyst comprises a supported organo-zirconium catalyst.

6. The method of claim 1, wherein selectivity to cis-substituted cyclohexanes is greater than about 90%.

7. The method of claim 6, wherein the selectivity to cis-substituted cyclohexanes is greater than about 95%.

8. The method of claim 7, wherein the selectivity to cis-substituted cyclohexanes is essentially 100%.

9. The method of claim 1, wherein the supported organometallic hydrogenating catalyst comprises Cp*ZrBz$_2$/ZrS where:
   Cp* is a pentamethylcyclopentadienyl,
   Bz is a benzyl or substituted benzyl,
   Zr is zirconium, and
   ZrS is a sulfated zirconia support.

10. A method for stereoselective hydrogenation of substituted arenes comprising the step of:
    contacting a reaction stream comprising one or more substituted arenes with hydrogen in the presence of a supported organozirconium hydrogenating catalyst under reaction conditions effective to selectively hydrogenate the substituted arenes to produce a product stream, wherein the product stream is selective to cis-substituted cyclohexanes when the reaction stream comprises two or more substituted arenes wherein the supported organometallic hydrogenating catalyst comprises a catalytically active organometallic species with the general formula of $Cp^{\#}_c ZrR_r$, and a Brønsted acidic sulfated metal oxide support, where $Cp^{\#}$ indicates a cyclopentadienyl ligand selected from the group consisting of cyclopentadienyl (Cp), pentamethylcyclopentadienyl (Cp*), a cyclopentadienyl radical substituted with alkyl or trimethylsilyl groups, and a fused cyclopentadienyl radical; c is from 1 to 2; Zr is zirconium; R is an alkyl or aromatic ligand selected from the group consisting of benzyl or substituted benzyl (Bz), phenyl or substituted phenyl (Ph), 2,2-dimethylpropyl (neopentyl) or substituted 2,2-dimethylpropyl, trimethylsilylmethyl (neosilyl) or substituted trimethylsilymethyl, and 2,2-dimethylethylbenzyl (neophyl) or substituted 2,2-dimethylethylbenzyl; and r is determined by the equation r=4−c.

11. The method of claim 10, wherein the substituted arenes are selected from the group consisting of di-alkyl arenes, tri-alkyl arenes, bicyclic arenes, and/or mixtures thereof.

12. The method of claim 11, wherein the substituted arenes are selected from the group consisting of xylenes, trimethylbenzenes, naphthalenes, and/or mixtures thereof.

13. The method of claim 10, wherein selectivity to cis-substituted cyclohexanes is greater than about 90%.

14. The method of claim 13, wherein the selectivity to cis-substituted cyclohexanes is greater than about 95%.

15. The method of claim 14, wherein the selectivity to cis-substituted cyclohexanes is essentially 100%.

16. A method for stereoselective hydrogenation of substituted arenes comprising the step of:

contacting a reaction stream comprising substituted arenes selected from the group consisting of di-alkyl arenes, tri-alkyl arenes, bicyclic arenes, and/or mixtures thereof with hydrogen in the presence of a heterogeneous hydrogenating catalyst under reaction conditions effective to deliver hydrogen selectively to one face of the substituted arenes, yielding a product stream comprising cis-substituted cyclohexanes, wherein selectivity to cis-substituted cyclohexanes is greater than about 95%, and wherein the heterogeneous hydrogenating catalyst comprises Cp*ZrBz$_2$/ZrS, where:

Cp* is a pentamethylcyclopentadienyl,

Bz is a benzyl or substituted benzyl,

Zr is zirconium, and

ZrS is a sulfated zirconia support.

17. The method of claim 16, wherein the selectivity to cis-substituted cyclohexanes is essentially 100%.

18. The method of claim 1, wherein the Brønsted acidic sulfated metal oxide support is selected from the group consisting of sulfated alumina (AlS), sulfated zirconia (ZrS) and tungstated zirconia (ZrW).

19. The method of claim 10, wherein the Brønsted acidic sulfated metal oxide support is selected from the group consisting of sulfated alumina (AlS), sulfated zirconia (ZrS) and tungstated zirconia (ZrW).

* * * * *